United States Patent [19]

Aberg et al.

[11] Patent Number: 6,068,833
[45] Date of Patent: May 30, 2000

[54] METHODS AND COMPOSITIONS FOR TREATING PULMONARY DISORDERS USING OPTICALLY PURE (R,R) FORMOTEROL

[75] Inventors: Gunnar Aberg, Westborough, Mass.; John Morley, Kew, United Kingdom

[73] Assignee: Sepracor Inc., Marlborough, Mass.

[21] Appl. No.: 09/136,109

[22] Filed: Aug. 18, 1998

Related U.S. Application Data

[63] Continuation of application No. 08/613,382, Mar. 7, 1996, Pat. No. 5,795,564, which is a continuation-in-part of application No. 08/373,515, Jan. 12, 1995, abandoned, which is a continuation-in-part of application No. 08/222,319, Apr. 4, 1994, abandoned, which is a continuation of application No. 07/927,458, Aug. 10, 1992, abandoned, and a continuation-in-part of application No. 08/382,744, Feb. 2, 1995, abandoned, which is a continuation of application No. 08/223,798, Apr. 6, 1994, abandoned, which is a continuation of application No. 07/862,907, Apr. 3, 1992, abandoned.

[30] Foreign Application Priority Data

Apr. 5, 1991 [GB] United Kingdom .................... 9107196

[51] Int. Cl.$^7$ ...................................................... A61K 9/12
[52] U.S. Cl. .............................. 424/45; 424/46; 424/449; 514/826; 514/937
[58] Field of Search ................................ 424/449, 45, 46; 514/826, 937

[56] References Cited

U.S. PATENT DOCUMENTS

| | | | |
|---|---|---|---|
| 3,994,974 | 11/1976 | Murakami | 280/562 A |
| 4,380,534 | 4/1983 | Fukui | 424/38 |
| 4,814,161 | 3/1989 | Jinks | 424/45 |
| 4,917,676 | 4/1990 | Heiber | 424/449 |
| 4,975,466 | 12/1990 | Bottcher | 514/630 |
| 5,135,954 | 8/1992 | McDonald | 514/630 |
| 5,362,755 | 11/1994 | Barberich | 514/649 |

FOREIGN PATENT DOCUMENTS

| | | | |
|---|---|---|---|
| 2255503 | 11/1992 | United Kingdom . | |
| 92/05147 | 2/1992 | WIPO . | |
| 92/05147 | 4/1992 | WIPO | C07C 231/14 |

OTHER PUBLICATIONS

"Steric Aspects of Agonism and Antagonism at B–Adrenoceptors: Synthesis of and Pharmacological Experiments with the Enantiomers of Formoterol and Their Diastereomers", Trofast et al., Chirality, 3, 443–450 1991).

"Comparison of the Action of BD 40 A and some Other β–Adrenoceptor Stimulants of the Isolated Trachea and Atria of the Guinea Pig" H. Ida Arzneim.–Forsch. 26, 839–842 (1976).

"Cardiorespiratory Activities of 3–Formylamino–4–hydroxy α–(N–1–methyl–2–methoxyphenethylaminomethyl)–benzylalcohol–bemifumarate (BD 40A) and some other β–Adrenoceptor Stimulants in Conscious Guinea Pigs" H. Ida Arzneim.–Forsch. 26, 1337–1340 (1976).

"New β–Adrenoreceptor Stimulants. Studies on 3–Acylamino–4–hydroxy–α–(N–substituted aminomethyl–)benzyl Alcohols" Murase et al. Chem. Pharm. Bull. 25(6) 1368–1377 (1977).

"A Three–Month Comparison of Twice Daily Inhaled Formoterol Versus Four Times Daily Inhaled Albuterol in the Management of Stable Asthma [1–3]" Kesten et al. Am. Rev. Respir. Dis. 144 622–625 (1991).

"Absolute Configurations of Four Isomers of 3–Formamido–4–hydroxy–. . . " Murase et al., Chem. Pharm. Bull. 26, 1123–29 (1978).

"β–Adrenoceptor Ligands: Characterization and Quantification of Drug Effects" Lemoine Quant. Struct.–Act. Relat. 11, 211–218 (1992).

"Stereoselectivity in pharmacodynamics and pharmacokinetics" Ariëns Schjweiz. med. Wochenschr. 120, 131–134 (1990).

"Racemic therapeutics–ethical and regulatory aspects" Ariëns Eur. J. Clin. Pharmacol 41, 89–93 (1991).

"Racemates Versus Enantiomers in Drug Development: Dogmatism . . . " Testa et al. Chirality 2, 129–133 (1990).

Murase et al. "Absolute Configurations of Four Isomers of 3–Formamido–4–hydroxy–. . . " Chem. Pharm. Bull. 26, 1123–1129 (1978).

Horst Lemoine "β–Adrenoceptor Ligands: Characterization and Quantification of Drug Effects" Quant. Struct.–Act. Relat. 11, 211–218 (1992).

E.J. Ariens, "Racemische therapeutica probleemmiddelen" Pharmaceutisch Weekblad, 125, 552–554 (1990).

E.J. Ariens, "Stereoselectivity in Pharmacodynamics and Pharmacokinetics" Schweiz. Med. Wochenschr, 120; 131–134, (1990).

E.J. Ariens, Racemic Therapeutics–Ethical and Regulatory Aspects, Eur. J. Clin. Pharmacol, 41, 89–93, (1991).

Testa, Bernard and Trager, William, "Racemates Versus Enantiomers in Drug Development: Dogmatism or Pragmatism?" Chirality, 2, 129–133, (1990).

Primary Examiner—Raj Bawa
Attorney, Agent, or Firm—Heslin & Rothenberg, P.C.

[57] ABSTRACT

A method and composition are disclosed utilizing the pure (R,R) isomer of formoterol, which is a potent bronchodilator with reduced adverse effects, having a low incidence of the development of tolerance and having increased duration of action.

15 Claims, No Drawings

METHODS AND COMPOSITIONS FOR TREATING PULMONARY DISORDERS USING OPTICALLY PURE (R,R) FORMOTEROL

CROSS REFERENCE TO RELATED APPLICATIONS

This application is a continuation of earlier application, Ser. No. 08/613,382 filed Mar. 7, 1996, now U.S. Pat. No. 5,795,564, which was a continuation-in-part of earlier application, Ser. No. 08/373,515 filed Jan. 12, 1995, now abandoned, which was a continuation-in-part of application Ser. No. 08/222,319 filed Apr. 4, 1994, now abandoned, which was a continuation of application Ser. No. 07/927,458, filed Aug. 10, 1992, now abandoned. This application is also a continuation-in-part of application, Ser. No. 08/382,744 filed Feb. 2, 1995, now abandoned, which was a continuation of application Ser. No. 08/223,798 filed Apr. 6, 1994, now abandoned, which was a continuation of application Ser. No. 07/862,907, filed Apr. 3, 1992, now abandoned. The entire disclosures of these applications are incorporated herein by reference. Application Ser. No. 07/862,907 claims the priority, under 35 USC 119, of Great Britain application 9107196.9, filed Apr. 5, 1991.

BACKGROUND OF THE INVENTION

This invention relates to novel compositions of matter containing optically pure (R,R) formoterol. These compositions possess potent, long-lasting bronchodilating activity as β-adrenergic agonists while avoiding or reducing adverse effects including but not limited to muscle tremor and tachycardia as well as avoiding or reducing the development of tolerance or hypersensitivity on repeated administration. The compositions also provide an improved duration of action. This invention also relates to methods of treating asthma, bronchitis, emphysema, bronchospasms, and other ailments in patients with obstructive airway or allergic disorders while avoiding adverse effects, development of tolerance or hypersensitivity on repeated administration or a limited pattern of bronchial distribution when administered by inhalation.

The active compound of these compositions and methods is an optical isomer of formoterol, which is described by Ida in *Arzneim, Forsch*. 26, 839–842 and 1337–1340 (1976) and in U.S. Pat. No. 3,994,974. Chemically, the active compound is N-hydroxy-5-(1-hydroxy-2-[(2-(4-methoxyphenyl) methylethyl]amino]ethyl]phenylformamide, which exists as two enantiomeric pairs of diastereomers. Of these, the R,R diastereomer is the most active and, when substantially optically pure, will be hereinafter referred to as (R,R) formoterol. Formoterol is available commercially only as a racemic diastereomer, (R,R) plus (S,S) in a 1:1 ratio, and the generic name formoterol refers to this enantiomeric mixture. The racemic mixture of (±) formoterol that is commercially available for administration is a dihydrate of the fumarate salt.

When two chiral centers occur in the same molecule each of them can exist in two possible configurations. This gives rise to four combinations: (R,R), (S,S), (R,S) and (S,R). (R,R) and (S,S) are mirror images of each other and are therefore enantiomers which share chemical properties and melting points just like any other enantiomeric pair. (R,S) and (S,R) are similarly an enantiomeric pair. The mirror images of (R,R) and (S,S) are not, however, superimposable on (R,S) and (S,R). This relationship is called diastereomeric, and (R,R) is a diastereomer of (R,S). Formoterol, having two chiral centers, falls into this category.

Adrenergic or sympathomimetic drugs are so called because they are understood to exert their effect through their action on the body's adrenergic receptors of which there are three functionally divided types, the α, $\beta_1$ and $\beta_2$ receptors. On the basis of their interaction with these three receptor types, the adrenergic or sympathomimetic drugs are in turn classifiable into three groups:

1.1 Non-selective sympathomimetic drugs;
1.2 Non-selective β sympathomimetic drugs; and
1.3 Selective $\beta_2$ sympathomimetic bronchodilator drugs.

Drugs of group 1.1 exert both a and a sympathomimetic effects. They include the drug substances adrenaline and ephedrine. Both adrenaline and ephedrine are known clinically as bronchodilators. Though adrenaline, despite side effect induced via its α-sympathomimetic properties, is still used by some practitioners for the treatment of acute asthma, both adrenaline and ephedrine have been largely superseded in asthma therapy.

The drugs of group 1.2 have both $\beta_1$ and $\beta_2$ sympathomimetic activity but no, or only limited, α-sympathomimetic activity. Of the group 1.2 drugs, isoprenaline is the best known representative. Isoprenaline differs from the drugs of group 1.3 in its faster onset but shorter duration of action and its cardiac stimulating effects which result largely from its $\beta_1$ activity. Though isoprenaline has previously been extensively used as bronchodilator therapy in asthma, its use has today become clinically restricted. Thus, in the UK, a rise in the rate of asthma death in the 1960's believed to have been specifically associated with isoprenaline usage has resulted in discontinuation of its clinical application.

The selective $\beta_2$ sympathomimetic bronchodilator drugs of group 1.3 (herein referred to for convenience collectively as "Group 1.3 drugs") act, as their name implies, selectively on the $\beta_2$ adrenergic receptors. The Group 1.3 drugs include for example, the drug substances terbutaline, albuterol, fenoterol, isoetharine, metaproterenol and, more recently, the so-called "long acting selective $\beta_2$ sympathomimetic bronchodilator drug substances" formoterol, bambuterol and salmeterol. All of the above recited Group 1.3 drugs are commercially available and clinically used, generally in pharmaceutically acceptable salt form, e.,g. as the sulphate, hydrobromide, hydrochloride, fumarate or methanesulfonate or, where appropriate, one or other of the hydrate forms thereof.

Group 1.3 drugs characteristically contain as part of their structure an ethanolamine or 2-amino-ethanol moiety of formula I

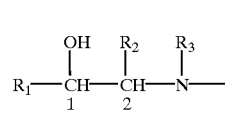

(I)

in which $R_1$ is an aromatic group. Commonly $R_1$ is 3,4- or 3,5-dihydroxyphenyl or 4-hydroxy-3-hydroxymethylphenyl. $R_1$ may also be 3-formylamino-4-hydroxyphenyl, as in the case of formoterol. $R_2$ and $R_3$ in formula I are commonly H. Since the formula I moiety comprises at least 1 asymmetric carbon atom (Cl in formula I), all of the Group 1.3 drugs exist in optically active isomeric form, with the chiral carbon atom having the (R) or (S) configuration [as designated using the Cahn-Ingold-Prelog system (Angew. Chem. Intern. Ed. 5, 385–415 (1966)]. When the Cl carbon atom is the sole asymmetric carbon atom present, Group 1.3 drugs thus exist as individual (R) or (S) enantiomers or in racemic [(RS)] form, i.e. as a 50:50 mixture of the (R) and (S) enantiomers.

Individual Group 1.3 drugs in which $R_2$ in the formula I moiety is other than H, or in which the remainder of the molecule includes an asymmetric carbon atom (e.g. formoterol) exist in a variety of isomeric forms, i.e. in individual (R,R), (S,S) (R,S) and (S,R) isomeric form, as racemic [(RS,RS) and (RS,SR)] mixtures comprising the (R,R) plus (S,S) and (R,S) plus (S,R) enantiomeric pairs, as well as in the form of diastereomeric mixtures comprising all four isomeric forms.

The Group 1.3 drugs can be administered orally, parenterally or (most commonly) by inhalation, e.g. using nebulizers or metered aerosol devices or as inhaled powders. Inhalation of Group 1.3 drugs presently represents the mainstay of bronchodilator therapy for the treatment of asthma of all grades of severity. The duration of bronchodilatation induced by the majority of Group 1.3 drugs is relatively short and they are employed to relieve asthma attack as and when it occurs. As indicated above, the more recently introduced Group 1.3 drugs, such as formoterol, are characterized by their longer duration of action and hence apparent reduced frequency of dosaging required.

Although the Group 1.3 drugs are effective and generally seem to be well tolerated, their safety, especially at high dosages, has been questioned over many years and numerous reports have appeared on the adverse effects of Group 1.3 drug therapy (see e.g. Paterson et al: *American Review of Respiratory Disease* 120, 844–1187 (1979) especially at page 1165 et seq.). More recently, from New Zealand, where a continuing increase in asthma death has been recorded, two case control studies reported in *The Lancet* have linked increase in asthma mortality to use of the Group 1.3 drug, fenoterol—see in particular: Editorial "$\beta_2$ agonists in asthma: relief, prevention, morbidity", *Lancet* 336, 1411–1412 (1990). A subsequently reported Canadian study finds that the use of inhaled Group 1.3 drugs, principally fenoterol and albuterol, is associated with "an increased risk of the combined outcome of fatal and near-fatal asthma, as well as of death from asthma alone"—see Spitzer et al., *New England J. Med.* 326 (8), 501–506 (1992) and the Editorial to the same issue at page 560.

Various possible explanations for observed episodes of increased airway obstruction, arterial hypoxaemia or "anomalous" or "paradoxical" bronchospasm, as well as increased morbidity associated with Group 1.3 drug usage, in particular long term/high dose usage, have been proposed. These have included, for example, reactive myogenic tone, increased inflammatory burden, adrenoceptor tachyphylaxis and induction of airway hyperreactivity, as well as the involvement of spasmogenic drug metabolic products or long term influence of aerosol spray propellants—see e.g. Paterson et al. loc. cit. and Morley et al., *Eur. Respir. J.* 3, 1–5 (1990).

There is mounting concern within the medical profession as to the potential dangers of Group 1.3 drug usage in asthma therapy. To quote the *Lancet* editorial already referred to:

"These studies raise serious question about the use of $\beta2$ agonists [i.e. Group 1.3 drugs]. The findings of Sears et al. could be interpreted as supporting the current trend towards earlier use of corticosteroids and other preventers of inflammation [for asthma therapy] rather than perseverance with an escalating bronchodilator regimen. The findings of the Nottingham and Dunedin groups also indicate that there is some way to go before long acting β2 agonist preparations such as salmeterol and formoterol can be unreservedly recommended for routine use in the management of asthma. There seem to be clear advantages of compliance and possibly of anti-inflammatory activity associated with such agents, but the potential for adverse effects cannot be ignored. Clinicians researchers and pharmaceutical companies must now attempt to redefine the use of β2 agonists in asthma." [Emphasis added.]

Equally there has been evident inability or reluctance to conceive of any problem in relation to Group 1.3 drug therapy as being inherent in Group 1.3 drugs themselves or as hitherto employed—cf. the following, taken from the editorial in the *New England Journal of Medicine* also previously referred to:

"Although . . . too much reliance is placed on beta-agonists (Group 1.3 drugs], it is difficult to believe that the problem is related directly to the more regular use of inhaled beta-agonists.

While the suitability, in particular of high-dose or long-term, Group 1.3 drug therapy has long been a subject of debate and, more recently, acute question, the practice of administering drugs of this group as racemic mixtures has continued. This practice has been accepted by drug registration authorities world-wide and even the most recently introduced of the Group 1.3 drugs have been developed for clinical use as racemic mixtures. This practice is based upon the assumption or understanding that the non-bronchodilator component of the racemic mixture, i.e. the bronchodilatorily less or inactive enantiomer (distomer) is devoid of any relevant drug effect and can thus be administered together with the bronchodilatorily active isomer (eutomer) essentially as inactive ballast and without risk to the patient. The teaching of the present invention thus stands in stark opposition to long, widely established and continuing practice. The present invention thus runs contrary to the wisdom of the art. In that the Group 1.3 drugs clearly offer very considerable potential benefit for bronchodilator usage in asthma, the need to find a means of avoiding, ameliorating or restricting disadvantages inherent in their use is urgent and crucial. By meeting this need, the present invention may be anticipated to bring immeasurable benefit both to the medical profession and the world asthma population.

Formoterol, which is the subject of the present invention, is available only as a racemic mixture of the (R,R) and (S,S) diastereomers. Trofast et al. [Chirality 3, 443–450 (1991)] have described the preparation of each of the substantially pure isomers. They concluded that "Since the (S,S)-enantiomer is practically inactive there is from this point of view no reason for its removal from the racemate in pharmaceutical preparations . . ."

Formoterol's primary use is as a long-acting bronchodilator for the relief of reversible bronchospasm in patients with obstructive airway disease such as asthma, bronchitis and emphysema.

Asthma, bronchitis and emphysema are known as Chronic Obstructive Pulmonary Diseases (COPD). COPD is characterized as generalized airways obstruction, particularly of small airways, associated with varying degrees of symptoms of chronic bronchitis, asthma, and emphysema. The term COPD was introduced because these conditions often coexist, and it may be difficult in an individual case to decide which is the major condition producing the obstruction. Airways obstruction is defined as an increased resistance to airflow during forced expiration. It may result from narrowing or obliteration of airways secondary to intrinsic airways disease, from excessive collapse of airways during a forced expiration secondary to pulmonary emphysema, from bronchospasm as in asthma, or may be due to a combination of these factors. Although obstruction of large airways may occur in all these disorders, particularly in asthma, patients with severe COPD characteristically have major abnormalities in their small airways, namely those less than 2 mm internal diameter, and much of their airways obstruction is situated in this zone. The airways obstruction is irreversible except for that which can be ascribed to asthma.

Asthma is a reversible obstructive lung disorder characterized by increased responsiveness of the airways. Asthma can occur secondarily to a variety of stimuli. The underlying mechanisms are unknown, but inherited or acquired imbalance of adrenergic and cholinergic control of airways diameter has been implicated. Persons manifesting such imbalance have hyperactive bronchi and, even without symptoms, bronchoconstriction may be present. Overt asthma attacks may occur when such persons-are subjected to various stresses, such as viral respiratory infection, exercise, emotional upset, nonspecific factors (e.g., changes in barometric pressure or temperature), inhalation of cold air or irritants (e.g., gasoline fumes, fresh paint and noxious odors, or cigarette smoke), exposure to specific allergens, and ingestion of aspirin or sulfites in sensitive individuals. Psychologic factors may aggravate an asthmatic attack but are not assigned a primary etiologic role.

Persons whose asthma is precipitated by allergens (most commonly airborne pollens and molds, house dust, animal danders) and whose symptoms are IgE-mediated are said to have allergic or "extrinsic" asthma. They account for about 10 to 20% of adult asthmatics; in another 30 to 50%, symptomatic episodes seem to be triggered by nonallergenic factors (e.g., infection, irritants, emotional factors), and these patients are said to have nonallergic or "intrinsic" asthma. In many persons, both allergenic and nonallergenic factors are significant. Allergy is said to be a more important factor in children than in adults, but the evidence is inconclusive.

Chronic bronchitis (unqualified) is a condition associated with prolonged exposure to nonspecified bronchial irritants and accompanied by mucus hypersecretion and certain structural changes in the bronchi. Usually associated with cigarette smoking, it is characterized clinically by chronic productive cough. The term chronic obstructive bronchitis is used when chronic bronchitis is associated with extensive abnormalities of the small airways leading to clinically significant airways obstruction. (Pulmonary emphysema is enlargement of the air spaces distal to terminal nonrespiratory bronchioles, accompanied by destructive changes of the alveolar walls.) The term chronic obstructive emphysema is used when airways obstruction is also present and where it is clear that the major features of the disease can be explained by emphysematous changes in the lungs.

Many of the $\beta_2$ agonists cause somewhat similar adverse effects. These adverse effects include but are not limited to the central nervous system symptoms such as hand tremors, muscle tremors, nervousness, dizziness, headache and drowsiness; respiratory side effects such as dyspnea, wheezing, drying or irritation of the oropharynx, coughing, chest pain and chest discomfort; cardiovascular effects such as palpitations, increased heart rate, and tachycardia. According to Trofast et al. (op. cit.) (R,R) formoterol is primarily a chronotropic agent in vitro with inotropic effects showing up at higher concentrations. The chronotropic effects are reported at concentrations that are higher than those at which relaxation of tracheal muscle (bronchodilation) is seen. β-Agonists (e.g. dobutamine) are known in general to exhibit inotropic activity. In addition, racemic $\beta_2$-agonists can cause angina, vertigo, central stimulation and insomnia, airway hyperreactivity (hypersensitivity), nausea, diarrhea, dry mouth and vomiting. As with other pharmaceuticals $\beta_2$-agonists sometimes cause systemic adverse effects such as weakness, fatigue, flushed feeling, sweating, unusual taste, hoarseness, muscle cramps and backaches.

Furthermore, patients have a tendency to develop a tolerance to the bronchodilating effect of the racemic mixture of formoterol. This is related to desensitization, which is one of the most clinically significant phenomena involving the beta-adrenergic receptor. It has been observed that patients in prolonged beta-agonist therapy have a tendency to increase the dosage of drug they use. This occurs because after prolonged administration, the beta-receptor appears to become desensitized to the agonist, thus requiring larger doses of the compound to effect an equivalent physiological response.

The problem of desensitization is especially significant in the treatment of diseases involving bronchospasms, such as asthma. The treatment of asthma usually involves the self-administration either orally or by aerosol, of beta-adrenergic agonists such as the racemic (R,R) (S,S) mixture of formoterol. These agonists mediate bronchodilation and promote easier breathing. Asthmatic patients utilizing β-agonists for a prolonged time gradually increase the self-administered dose in order to get a sufficient amount of bronchodilation and relief in breathing. As a result of this increased dosage, the agonist concentration builds to a sufficient level so as to enter the peripheral circulation where it acts on the beta receptors of the heart and vasculature to cause cardiovascular stress and other adverse effects.

Moreover, when administering the racemic mixture of formoterol by inhalation, because of particle size and air flow distribution characteristics of the racemic mixture of formoterol, the distribution of the compound into the smaller bronchioles is limited, which results in a decreased effectiveness of the compound.

It is therefore desirable to find a compound with the therapeutic characteristics of formoterol which would not have the above described disadvantages.

SUMMARY OF THE INVENTION

It has now been discovered that the (R,R) isomer of formoterol is an effective bronchodilator that does not have certain adverse effects associated with the administration of the racemic mixture of (R,R) and (S,S) formoterol. The present invention includes administering to a human (R,R) formoterol to cause bronchodilation and to decrease said adverse effects. Furthermore, it has also been discovered that by administering only the (R,R) isomer of formoterol there is decreased tolerance and hypersensitivity to the compound, relative to that seen when the racemic mixture of formoterol is administered. In addition, it has been discovered that by administering the (R,R) isomer of formoterol by inhalation, it is possible to obtain improved distribution of the compound in the smaller bronchioles which results in an increased bronchodilating effect. In addition, an increased duration of the beneficial effects is observed upon administration of the substantially pure (R,R) enantiomer, as compared to administration of the racemic drug.

The present invention also includes novel compositions of matter containing optically pure (R,R) formoterol which is useful as a bronchodilator. These novel compositions also avoid the above described adverse effects, increased tolerance or limited pattern of distribution when administered by inhalation, associated with the racemic mixture of formoterol.

DETAILED DESCRIPTION OF THE INVENTION

The present invention encompasses a method of eliciting a bronchodilator effect while avoiding the concomitant liability of adverse effects, development of tolerance, or limited pattern of bronchial distribution when administered by inhalation, which comprises administering to a human in need of bronchodilation an amount sufficient to alleviate bronchospasms, but insufficient to cause said adverse effects, development of tolerance, hypersensitivity or limited pattern of bronchial distribution when administered by inhalation, of (R,R) formoterol or a pharmaceutically acceptable salt thereof, substantially free of its (S,S) stereoisomer. The bronchodilator effects are achieved by utilizing the highly potent β-adrenergic effects of the (R,R) isomer of formoterol while substantially limiting the adverse effects, development of tolerance, hypersensitivity or limited pattern of bronchial distribution when administered by inhalation, by decreasing or eliminating the amount of (S,S) isomer in the composition.

As hereinbefore described in relation to formula I, Cl in the eutomer of Group 1.3 drugs characteristically has the (R) configuration. In the case of Group 1.3 drugs having two asymmetric carbon atoms, the eutomer could thus be the (R,R) or (R,S) isomer. Although we have found that it is the (R,R) enantiomer which has the greatest bronchodilator potency, Group 1.3 drugs having two asymmetric carbon atoms have hitherto been used in the clinic generally in the form of the (RS,RS) racemic mixture.

The present invention also encompasses a bronchodilator composition for the treatment of a patient in need of bronchodilating therapy which comprises an amount sufficient to alleviate bronchospasms but insufficient to cause adverse effects, development of tolerance or limited bronchial distribution when administered by inhalation, of (R,R) formoterol or a pharmaceutically acceptable salt thereof, substantially free of its (S,S) stereoisomer.

The racemic mixture of formoterol causes bronchial smooth muscle relaxation and modulates inhibition of mediator release effect; however, this racemic mixture causes adverse effects, leads to the development of tolerance and the development of hypersensitivity and results in a limited pattern of bronchial distribution when administered by inhalation. Utilizing the (R,R) isomer of formoterol results in diminished adverse effects, decreased development of tolerance and increased bronchial distribution when the compound is administered by inhalation. Thus, it is much more desirable to use the (R,R) isomer of formoterol when treating asthma, bronchitis, emphysema or to alleviate bronchospasms.

Furthermore, although there is some variability from one patient to another, it is generally observed that, by administering an effective amount of only the (R,R) isomer of formoterol it is possible to accomplish a more "targeted" therapy. A more "targeted" therapy means that by using the (R,R) isomer the compound's activity can be taken advantage of without also having consequences of the pharmacologic effects of the (S,S) isomer which are observed upon administration of the racemic mixture. This is important since it is not desirable for all patients to be administered a compound with such a multifaceted spectrum of activity.

The present invention provides a method or use for the treatment of inflammatory airways disease, in particular for effecting bronchodilatation, e.g. as a means of alleviating airways obstruction, in particular acute airways obstruction, e.g. asthma attack, occurring in such disease. The invention thus provides symptomatic, rather than prophylactic, therapy for such disease. The teaching of the present invention is applicable in the therapy of inflammatory or obstructive airways disease, in particular any such disease for which Group 1.3 drug therapy is commonly practiced, for example chronic obstructive pulmonary disease, e.g. consequential to cystic fibrosis, emphysema and, especially, chronic bronchitis and, most especially, asthma.

The present invention avoids deleterious side effects hereinbefore resulting or observed in, e.g. asthmatic, patients consequent to conventional clinical usage of Group 1.3 drugs as racemic mixtures. In particular the invention provides means to avoid, ameliorate or restrict deleterious side effects, e.g. side effects deleterious to the airways. Thus the invention provides means to avoid, ameliorate or restrict exacerbation of disease status, for example basal disease, e.g. basal asthmatic, status or to avoid, ameliorate or restrict compromise or deterioration of lung function, or any other side effect concomitant to conventional clinical usage, for example "anomalous", "rebound" or "paradoxical,, bronchospasm and, especially, increase in airway obstruction, exacerbation of late asthmatic response or non-specific bronchial reactivity or arterial hypoxemia. Without limiting the present invention to any specific theory or mode of action, the present invention is in particular to be understood as providing a means for the avoidance, amelioration or restriction of exacerbation of airways hyperreactivity and/or of an inflammatory or other event associated with, or which is an etiological component of, inflammatory or obstructive airways disease, e.g. asthma. Such events are to be understood as including for example, inflammatory cell infiltration of the lungs or airways, connective tissue deposition or smooth muscle hyperplasia within the lungs or airways or other morphological change associated with asthmatic status. The present invention also provides a means of preventing or reducing morbidity, e.g. asthma morbidity, ascribable to conventional, e.g. high dosage or long term, Group 1.3 drug usage.

The present invention is especially applicable in the therapy of bronchial asthma of whatever type or genesis. It is applicable to both intrinsic and extrinsic asthma. It is especially applicable to the treatment of allergic or atopic (i.e. IgE-mediated) asthma or non-atopic asthma, as well as exercise induced asthma, occupational asthma, asthma induced following bacterial infection or drug, e.g. aspirin, ingestion and other non-allergic asthmas. Treatment of asthma is also to be understood as embracing treatment of subjects, e.g. of less than 4 or 5 years of age, exhibiting chronic cough or wheezing symptoms, in particular at night, and diagnosed or diagnosable as "wheezy infants", i.e. as embracing the treatment of "wheezy infant syndrome". other diseases to which the present invention is in particular applicable include for example chronic obstructive pulmonary or airways disease (COPD or COAD).

The term "adverse effects" includes but is not limited to hand tremors, muscle tremors, nervousness, palpitations, tachycardia, increased heart rate, dyspnea, coughing, chest pain, chest discomfort, drying or irritation of the oropharynx and wheezing. Also included in the term "adverse effects" are headaches, dizziness, fatigue, hoarseness, backaches, nausea, vomiting, drowsiness, weakness, flushed feeling, sweating, unusual taste, muscle cramps, weakness, angina, vertigo, central stimulation, hypersensitivity and insomnia.

The term "substantially free of the (S,S) stereoisomer" as used herein means that the composition contains at least about 90% by weight of (R,R) formoterol and 10% or less by weight of (S,S) formoterol. In a more preferred embodiment the composition contains at least 99% by weight (R,R) formoterol and 1% or less of (S,S) formoterol. In the most preferred embodiment the composition contains greater than 99% by weight of (R,R) formoterol and less than 1% by weight of (S,S) formoterol.

The term "eliciting a bronchodilator effect" means relief from the symptoms associated with obstructive airway diseases, which include but are not limited to respiratory distress, wheezing, coughing, shortness of breath, tightness or pressure in the chest and the like.

The term "development of tolerance" means that when administering the racemic mixture of formoterol in repeated dosage or over a period of time, the amount of the compound given to the patient must be increased in order to achieve the same effect as the lower dosage given at an earlier time.

The term "limited pattern of bronchial distribution when administered by inhalation" means that therapeutically efficacious quantities cannot penetrate into smaller bronchioles.

The mixture of formoterol isomers can be prepared according to U.S. Pat. No. 3,994,974. The diasteromers may be separated as described by Murase et al. [*Chem. Pharm. Bull.* 25, 1368-13 (1977). The individual isomers of formoterol may be obtained as described by Trofast et al. (op. cit.) by stereocontrolled synthesis from optically active starting material or by resolution of a mixture of enantiomers (i.e., the racemic mixture) using conventional means, such as an optically active resolving acid. Other standard methods of resolution known to those skilled in the art including but not limited to simple crystallization and chromatographic resolution can be used. (See for example, *Stereochemistry of Carbon Compounds,* E. L. Eliel, McGraw Hill 1962; "Tables of Resolving Agents," S. A. Wilen and Lochmuller, L. H. et al., 1975, *J. Chromatoqr.* 113(3): 283–302.) Additionally, the optically pure (R,R) isomer can be prepared from the racemic mixture by enzymatic biocatalytic resolution. See, for example, U.S. Pat. Nos. 5,057,427 and 5,077,217, the disclosures of which are incorporated herein by reference.

The magnitude of a prophylactic or therapeutic dose of (R,R) formoterol in the acute or chronic management of disease will vary with the severity of the condition to be treated, and the route of administration. The dose, and perhaps the dose frequency, will also vary according to the age, body weight, and response of the individual patient. In general, the total daily dose ranges when administered by inhalation, for the conditions described herein, is from about 1 $\mu$g to about 100 $\mu$g, in single or divided doses. Preferably, a daily dose range should be between about 6 $\mu$g to about 25 $\mu$g, in single or divided doses, while most preferably, a daily dose range should be between about 12 $\mu$g to about 25 $\mu$g, in from two to four divided doses. In managing the patient, the therapy should be initiated at a lower dose, perhaps about 3 $\mu$g to about 12 $\mu$g, and increased up to about 2×12 $\mu$g or higher depending on the patient's global response. When administered orally, preferably as a tablet, the preferred dose range is from 0.1 to 1.0 mg per day. It is further recommended that children, and patients over 65 years, and those with impaired renal, or hepatic function, initially receive low doses, and that they be titrated based on individual responses) and blood level(s). It may be necessary to use dosages outside these ranges in some cases as will be apparent to those skilled in the art. Further, it is noted that the clinician or treating physician would know how and when to interrupt, adjust, or terminate therapy in conjunction with individual patient response.

The terms "an amount sufficient to alleviate bronchospasms but insufficient to cause said adverse effects" are encompassed by the above-described dosage amounts and dose frequency schedule.

Any suitable route of administration may be employed for providing the patient with an effective dosage of (R,R) formoterol. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise (R,R) formoterol as the active ingredient, or a pharmaceutically acceptable salt thereof, and may also contain a pharmaceutically acceptable carrier, and optionally, other therapeutic ingredients.

The term "pharmaceutically acceptable salts" or "a pharmaceutically acceptable salt thereof" refer to salts prepared from pharmaceutically acceptable non-toxic acids including inorganic acids and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. The fumaric acid salt is particularly preferred.

The compositions of the present invention include compositions such as suspensions, solutions and elixirs; aerosols; or carriers such as starches, sugars, microcrystalline cellulose, diluents, granulating agents, lubricants, binders, disintegrating agents, and the like. The compositions include compositions suitable for oral, rectal, parenteral (including subcutaneous, transdermal, intramuscular, and intravenous) and inhalation, although the most suitable route in any given case will depend on the condition being treated and the nature and severity of that condition. The most preferred routes of the present invention are: (1) oral by either tablets or capsules, (2) inhalation and (3) transdermal by patch. They may be conveniently presented in unit dosage form and prepared by any of the methods well-known in the art of pharmacy.

In addition to the common dosage forms set out above, the compounds of the present invention may also be administered by controlled release means and/or delivery devices such as those described in U.S. Pat. Nos.: 3,845,770; 3,916, 899; 3,536,809; 3,598,123; and 4,008,719, the disclosures of which are hereby incorporated by reference.

The invention is further defined by reference to the following examples describing in detail the pharmacological characterization of the compound, and the preparation of compositions of the present invention. It will be apparent to those skilled in the art, that many modifications, both to materials, and methods, may be practiced without departing from the purpose and interest of this invention.

EXAMPLES

PROCEDURE 1

$\beta$-Adrenergic Receptor Phosphorylation by $\beta$-Adrenoreceptor Kinase. Reconstituted $\beta$-adrenergic receptor is incubated with $\beta$-adrenoreceptor kinase in a buffer containing 20 mM Tris-HCl, pH 7.5, 2 mM EDTA, 20 mM NaCl, 6 mM MgCl$_2$, 6 mM sodium phosphate, 0.5 mM ascorbic acid 60 $\mu$M [$\gamma^{-32}$P]ATP at 30° C. The incubations also contain varying concentrations of one of the following: buffer (control), (−)-isoproterenol, R,R-formoterol, S,S- formoterol or racemic formoterol. The incubations are stopped by the addition of SDS sample buffer followed by electrophoresis on 10% homogeneous polyacrylamide gels. Stoichiometries of phosphorylation are determined by cutting and counting the dried gel as described in Benovic J. L. et al. [*J. Biol. Chem.* 9026–9032 (1987)].

PROCEDURE 2

Purification of component proteins. The β-adrenergic receptor from hamster lung is purified to >95% homogeneity by sequential affinity chromatography and high performance liquid chromatography as described by Benovic et al. [*Biochemistry* 23, 4510–4518 (1984)]. The stimulatory guanine nucleotide regulatory protein is purified from membranes derived from bovine cerebral cortex. The membranes, solubilized with 1% cholate, are centrifuged and the resulting supernatant chromatographed on DEAE-Sephacel, Ultrogel AcA34, octyl-Sepharose, and hydroxyapatite, with a final step on DEAE-Sephacel, as adapted from Strittmater and Neer [*Proc. Natl. Acad. Sci.* 77, 6344–6348 (1980)]. The resulting protein should be 50–90% pure by Coomassie Blue staining of polyacrylamide gels. The catalytic moiety of adenylate cyclase is solubilized from bovine caudate with sodium cholate and isolated from the other components of the system by Sepharose 6B chromatography as described in Strittmater and Neer (op. cit.). β-Adrenoreceptor kinase is purified from bovine cerebral cortex. The tissue is homogenized, and the resulting high speed supernatant fraction is precipitated with 13–26% ammonium sulfate. This material is then chromatographed on Ultrogel AcA34, DEAE-Sephacel, and CM-Fractogel- The preparations used should be 10–20% pure as judged by Coomassie Blue staining of SDS-polyacrylamide gels.

Assay for adenylate cyclase activity. The co-reconstitution of the purified proteins is carried out as described in Cerione et al. *J. Biol. Chem.* 259, 9979–9982 (1984). The pelleted proteins are incubated for 15 min. at 37° C. in 30 mM Tris-HCl, pH 7.5 containing 1 mM ATP, 2 $\mu$Ci of [$\beta$-$^{32}$p]ATP 0.14 mM cAMP, 100 mM sucrose, 0.4 mM dithiothreitol, 2.8 mM phosphoenol pyruvate, 5.2 $\mu$g/mL pyruvate kinase, 10 $\mu$g/ml of myokinase, 5 mM MgCl$_2$, and varying concentrations of racemic formoterol, (R,R) formoterol and (S,S) formoterol (total volume=0.5 mL). The reaction is stopped by the addition of 0.25 mL 2% sodium dodecylsulfate containing 40 mM ATP and 1.4 m.M cAMP at pH 7.5. Water (0.5 mL) is added to each reaction tube and the contents placed on a Dowex 50AG WX4 resin. The eluate from the columns plus two successive water washes (1.0 mL) are discarded. The columns are then eluted with 3 mL water and the eluates collected in test tubes. Each fraction is diluted with 0.2 mL of 1.5 M imidazole HCl, pH 7.2. The tubes from each concentration (run in triplicate) are combined and decanted into columns containing 0.6 g neutral alumina that has been previously washed with 0.1 M imidazole HCl, pH 7.5. The eluate is collected in scintillation vials containing 12 mL Aquasol®. After the columns are completely drained, they are washed with an additional 1 mL of 0.1 M imidazole HCl, pH 7.5 which is collected in the same scintillation vials. The concentration of $^{32}$P-cAMP is determined in each sample.

The metabolic rates of the racemate and the isomers of formoterol have been studied in human liver tissues. It was unexpectedly found that the metabolic rate is significantly slower for (R,R) formoterol than for the racemate and for the SS-isomer. These new findings show that the clearance ($V_{max}/K_m$) was 152 for (R,R) formoterol, 381 for (S,S) formoterol and 489 for (R,R/S,S) formoterol. It is possible to calculate the relative biological half-lives ($t_{1/2}$) of the RR-isomer and the racemate from these data, using the formula Cl=Vd×0.693/$t_{1/2}$. Assuming the same distribution volume [Vd =1] for all three compounds, the relative half-lives are 4.6 for (R,R) formoterol and 1.4 for (R,R/S,S) formoterol. Thus, the half-life of (R,R) formoterol is approximately three times longer than the half-life of the racemate. This demonstrates a significant advantage of the pure RR enantiomer in terms of its duration of action as well as diminution of side effects.

EXAMPLE 1

ORAL FORMULATION

| Tablets: | Quantity per Tablet (mg.) | |
|---|---|---|
| Formula | A | B |
| (R,R) formoterol | 0.12 | 0.25 |
| Lactose | 41.38 | 41.25 |
| Cornstarch | 3.0 | 3.0 |
| Water (per thousand Tablets)* | 30.0 ml | 30.0 ml |
| Cornstarch | 5.00 | 5.00 |
| Magnesium Stearate | 0.50 | 0.50 |
| | 50.00 | 50.00 |

*The water evaporates during manufacture

The formoterol is blended with the lactose until a uniform blend is formed. The smaller quantity of cornstarch is blended with the water to form the resulting cornstarch paste. This is then mixed with said uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine, using ¼ mesh stainless steel screen. The magnesium stearate is then blended and the resulting mixture is compressed into tablets of desired shape, thickness, hardness and disintegration.

EXAMPLE 2

ORAL INHALATION

| Formula | Quantity contained in Each Metered Dose Dispenser 7.5 mL (10.5 g) Canister |
|---|---|
| (R,R) formoterol | 1.8 mg |
| trichloromonofluoromethane | 5.16 g |
| dichlorodifluoromethane | 5.16 g |
| sorbitan trioleate | 0.105 g |

The metered dose dispenser contains micronized (R,R) formoterol fumarate dehydrate in suspension. Each actuation delivers 6 Ag of (R,R) formoterol fumarate dehydrate from the mouthpiece. Each canister provides about 300 inhalations.

What is claimed is:

1. A method of treating asthma, while reducing hypersensitivity, which comprises administering to a human suffering from asthma an amount of (R,R)-formoterol, or a pharmaceutically acceptable salt thereof, sufficient to result in bronchodilation, said (R,R)-formoterol containing at least 99% by weight of (R,R)-formoterol and less than 1% by weight of (S,S)-formoterol.

2. A method of providing relief from bronchospasms, while reducing hypersensitivity, which comprises administering to a human an amount of (R,R)-formoterol, or a pharmaceutically acceptable salt thereof, sufficient to diminish bronchospasms, said (RR)-formoterol containing at least 99% by weight of (R,R)-formoterol and less than 1% by weight of (S,S)-formoterol.

3. The method of claim 2 wherein (R,R) formoterol is administered by subcutaneous injection, intravenous infusion, inhalation, transdermal delivery or oral administration.

4. The method according to claim 3 wherein the amount administered by inhalation is about 1 $\mu$g to about 100 $\mu$g per day.

5. The method according to claim 3 wherein the amount administered orally is about 0.1 to about 1 mg per day.

6. The method according to claim 2 wherein (R,R) formoterol fumarate dihydrate is administered.

7. The method of claim 1 wherein (R,R) formoterol is administered by subcutaneous injection, intravenous infusion, inhalation, transdermal delivery or oral administration.

8. The method according to claim 7 wherein the amount administered by inhalation is about 1 $\mu$g to about 100 $\mu$g per day.

9. The method according to claim 7 wherein the amount administered orally is about 0.1 to about 1 mg per day.

10. The method according to claim 1 wherein (R,R) formoterol or pharmaceutically acceptable salt thereof is administered together with a pharmaceutically acceptable carrier.

11. A method according to claim 7 wherein (R,R) formoterol fumarate dehydrate is administered.

12. A method according to claim 8 wherein said amount is administered in divided doses from two to four times a day.

13. A bronchodilator composition in the form of a powder for inhalation which comprises a pharmaceutically acceptable carrier suitable for inhalation and an amount of (R,R)-formoterol, or a pharmaceutically acceptable salt thereof, sufficient to alleviate bronchospasms but insufficient to cause hypersensitivity, said (R,R)-formoterol containing at least 99% by weight of (R,R)-formoterol and less than 1% by weight of (S,S)-formoterol.

14. A composition according to claim 13 adapted for administration by inhalation wherein the amount of (R,R) formoterol is about 6 $\mu$g to about 25 $\mu$g.

15. A composition according to claim 13 which comprises (R,R) formoterol fumarate dihydrate.

* * * * *